(12) United States Patent
Serrero et al.

(10) Patent No.: US 9,750,837 B2
(45) Date of Patent: Sep. 5, 2017

(54) HAEMOSTATIC PATCH AND METHOD OF PREPARATION

(71) Applicant: Sofradim Production, Trévoux (FR)

(72) Inventors: Aurelie Serrero, Lyons (FR); Suzelei Montanari, Trevoux (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 14/421,200

(22) PCT Filed: Sep. 25, 2013

(86) PCT No.: PCT/EP2013/069957
§ 371 (c)(1),
(2) Date: Feb. 12, 2015

(87) PCT Pub. No.: WO2014/048982
PCT Pub. Date: Apr. 3, 2014

(65) Prior Publication Data
US 2015/0202342 A1     Jul. 23, 2015

(30) Foreign Application Priority Data

Sep. 25, 2012   (FR) ..................... 12 58965

(51) Int. Cl.
*A61L 15/28*     (2006.01)
*A61F 13/00*     (2006.01)
(Continued)

(52) U.S. Cl.
CPC ............... *A61L 15/28* (2013.01); *A61L 15/44* (2013.01); *A61L 15/64* (2013.01);
(Continued)

(58) Field of Classification Search
None
See application file for complete search history.

(56) References Cited

U.S. PATENT DOCUMENTS

| 1,187,158 A | 6/1916 | Mcginley |
| 3,054,406 A | 9/1962 | Usher |

(Continued)

FOREIGN PATENT DOCUMENTS

| CA | 1317836 C | 5/1993 |
| CN | 201879864 U | 6/2011 |

(Continued)

OTHER PUBLICATIONS

Australian Office Action issued Apr. 8, 2016 in corresponding Australian Patent Application No. 2013322689, 3 pages.
(Continued)

*Primary Examiner* — Paula L Craig

(57) ABSTRACT

The present invention relates to a haemostatic patch comprising a porous layer based on oxidized cellulose and a neutralized film based on chitosan, said film comprising a free face and a face fixed on one of the faces of the porous layer, and to the method of preparing said patch comprising the following steps: —a°) preparing a porous layer based on oxidized cellulose, —b°) preparing a film based on chitosan starting from an acidic aqueous solution of chitosan, —c°) fixing the film obtained in b°) on one face of the porous layer, —d°) neutralizing the film obtained in b°), —where step c°) can be carried out before or after step d°), characterized in that: the neutralizing step d°) comprises treatment of said film with a neutralizing composition comprising at least ethanol and ammonium hydroxide ($NH_4OH$).

22 Claims, 2 Drawing Sheets

(51) Int. Cl.

| | | |
|---|---|---|
| *A61L 15/44* | (2006.01) | |
| *A61L 15/64* | (2006.01) | |
| *C08L 5/08* | (2006.01) | |
| *C08L 1/04* | (2006.01) | |
| *B32B 37/00* | (2006.01) | |
| *B32B 37/12* | (2006.01) | |
| *B32B 37/24* | (2006.01) | |
| *B32B 38/16* | (2006.01) | |

(52) U.S. Cl.
CPC ...... *B32B 37/0038* (2013.01); *B32B 37/1284* (2013.01); *B32B 37/24* (2013.01); *B32B 38/162* (2013.01); *C08L 1/04* (2013.01); *C08L 5/08* (2013.01); *A61L 2400/04* (2013.01); *B32B 2305/026* (2013.01); *B32B 2317/18* (2013.01); *B32B 2535/00* (2013.01); *B32B 2555/00* (2013.01); *Y10T 156/10* (2015.01)

(56) References Cited

U.S. PATENT DOCUMENTS

| | | |
|---|---|---|
| 3,118,294 A | 1/1964 | Van Laethem |
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,308,663 A * | 5/1994 | Nakagawa ............ D06M 15/03 162/157.7 |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A | 11/1994 | de la Torre |
| 5,370,650 A | 12/1994 | Tovey et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,756,111 A * | 5/1998 | Yoshikawa ............ C08B 37/003 424/402 |
| 5,766,246 A | 6/1998 | Mulhauser et al. |
| 5,766,631 A | 6/1998 | Arnold |

(56) References Cited

U.S. PATENT DOCUMENTS

| | | | |
|---|---|---|---|
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,900,479 A * | 5/1999 | Glasser ............... C08B 37/003 536/124 |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |

(56) References Cited

U.S. PATENT DOCUMENTS

| | | |
|---|---|---|
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0064551 A1* | 5/2002 | Edwards ............... A61L 15/28 424/445 |
| 2002/0087174 A1 | 7/2002 | Capello |
| 2002/0095218 A1 | 7/2002 | Carr et al. |
| 2003/0055211 A1* | 3/2003 | Roberts ............... C08B 37/003 528/391 |
| 2003/0086975 A1 | 5/2003 | Ringeisen |
| 2003/0091851 A1* | 5/2003 | Khor ..................... C08J 5/18 428/532 |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0058013 A1* | 3/2004 | Taylor ................. A01N 59/16 424/618 |
| 2004/0059356 A1 | 3/2004 | Gingras |
| 2004/0101546 A1 | 5/2004 | Gorman et al. |
| 2004/0243043 A1* | 12/2004 | McCarthy ........... A61F 13/0203 602/46 |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0159732 A1* | 7/2006 | Cullen ................. A61L 15/325 424/445 |
| 2006/0172000 A1* | 8/2006 | Cullen ................. A61L 15/225 424/445 |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0032805 A1* | 2/2007 | Therin ................. A61F 2/0063 606/151 |
| 2007/0088391 A1 | 4/2007 | McAlexander et al. |

(56) References Cited

U.S. PATENT DOCUMENTS

| | | |
|---|---|---|
| 2007/0129736 A1 | 6/2007 | Solecki |
| 2007/0198040 A1 | 8/2007 | Buevich et al. |
| 2007/0237811 A1* | 10/2007 | Scherr ............... A61K 31/722 424/445 |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0181936 A1* | 7/2008 | Filatov ............... A61K 31/717 424/445 |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli Torelli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li |
| 2009/0318752 A1 | 12/2009 | Evans et al. |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2011/0311632 A1* | 12/2011 | Roorda ............... A61K 31/722 424/488 |
| 2012/0016388 A1 | 1/2012 | Houard et al. |
| 2012/0022242 A1* | 1/2012 | Domard ............... D01D 5/06 536/20 |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0093686 A1* | 4/2012 | Kirsch ............... A61L 15/28 422/23 |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell |
| 2012/0179176 A1 | 7/2012 | Wilson et al. |
| 2012/0197415 A1 | 8/2012 | Montanari et al. |
| 2013/0287836 A1* | 10/2013 | Ingber ............... C08L 5/08 424/443 |
| 2014/0044861 A1 | 2/2014 | Boey et al. |
| 2014/0364684 A1 | 12/2014 | Lecuivre |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 1 952 828 A2 | 8/2008 |
| EP | 2229918 A1 | 9/2010 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 9310731 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |

(56) References Cited

FOREIGN PATENT DOCUMENTS

| WO | 98/35632 A1 | 8/1998 |
|---|---|---|
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 01/81667 A1 | 11/2001 |
| WO | 02/07648 A1 | 1/2002 |
| WO | 0217853 A2 | 3/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023414 A2 | 3/2006 |
| WO | 2007048099 A2 | 4/2007 |
| WO | 2009031035 A2 | 3/2009 |
| WO | 2009071998 A2 | 6/2009 |
| WO | 2010043978 A2 | 4/2010 |
| WO | 2011026987 A1 | 3/2011 |
| WO | 2011038740 A1 | 4/2011 |
| WO | WO 2011/066471 A1 | 6/2011 |

OTHER PUBLICATIONS

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).
Malette, W. G. et al., "Chitosan, A New Hemostatic," Ann Th. Surg., Jul. 1983, pp. 55-58, 36.
Langenbech, M. R. et al., "Comparison of biomaterials in the early postoperative period," Surg Endosc., May 2003, pp. 1105-1109, 17 (7).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Klinge, U. et al., "Foreign Body Reaction to Meshes Used for the Repair of Abdominal Wall Hernias," Eur J. Surg, Sep. 1999, pp. 665-673, 165.
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Junge, K. et al., "Functional and Morphologic Properties of a Modified Mesh for Inguinal Hernia Repair," World J. Surg., Sep. 2002, pp. 1472-1480, 26.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern brown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Preliminary Search Report from French Patent Office dated Dec. 20, 2006, 3 pages.
Lamarque, G. et al, "New Route of Deacetylation of alpha- and beta-Chitins by Means of Freeze-Pump Out-Thaw Cycles" Biomacromolecules, May-Jun. 2005, pp. 1380-1388, 6.
Lamarque, G. et al., Comparative Study of the First Heterogeneous Deacetylation of alpha- and beta-Chitins in a Multistep Process Biomacromolecules May-Jun. 2004, 992-1001, 5.
Lamarque, G. et al., "Comparative Study of the Second and Third Heterogeneous Deacetylations of alpha- and beta-Chitins in a Multistep Process" Biomacromolecules, Sep.-Oct. 5, 2004, pp. 1899-1907, 5.
Tolaimate, A., et al. "Contribution to the preparation of chitins and chitosans with controlled physico-chemical properties." Polymer, Dec. 2003, pp. 7939-7952, 44 (26).
International Search Report for PCT/EP13/069957 date of completion is Feb. 25, 2014 (2 pages).

(56) References Cited

OTHER PUBLICATIONS

European Office Action issued Nov. 4, 2016 in corresponding European Patent Application No. 13766967.7, 5 pages.

* cited by examiner

HAEMOSTATIC PATCH AND METHOD OF PREPARATION

CROSS-REFERENCE TO RELATED APPLICATIONS

This application is a National Stage Application of PCT/EP13/069957 under 35USC §371 (a), which claims priority of French Patent Application Serial No. 12/58965 filed Sep. 25, 2012, the disclosures of each of the above-identified applications are hereby incorporated by reference in their entirety.

BACKGROUND

1. Technical Field

The present invention relates to a method of preparing a haemostatic patch comprising a porous layer, for example a textile, based on oxidized cellulose and a film based on neutralized chitosan fixed on one of the faces of the porous layer.

2. Description of Related Art

Haemostatic patches are implantable medical devices for stopping the flow of biological fluids such as blood during surgery. For this purpose, they are generally composed of an absorbent porous layer, which is intended to trap the biological fluids, and a barrier known as a haemostatic barrier, which is intended to block the passage of the biological fluids.

Some haemostatic patches can be completely bioabsorbable, i.e. they are made to disappear in vivo after implantation, after a few weeks for example, when their function of stopping the effusion of biological fluids is no longer necessary.

Oxidized cellulose is of interest as a bioabsorbable material that can constitute the absorbent porous layer of a haemostatic patch: in fact, oxidized cellulose possesses intrinsic haemostatic properties.

Chitosan is a polysaccharide obtained by deacetylation of chitin. Chitin is one of the most widespread naturally occurring polysaccharides and is extracted from the exoskeletons of arthropods, from the endoskeletons of cephalopods as well as from fungi.

Chitosan has properties, such as biodegradability, bioabsorbability, biocompatibility, non-toxicity, and mechanical properties, that make it particularly interesting for medical applications. Thus, it would be interesting to combine a porous layer of oxidized cellulose with a film based on chitosan with a view to preparing a haemostatic patch. Chitosan in fact offers a good compromise, taking into account the properties that are required, for a haemostatic barrier, namely good biocompatibility and good mechanical properties.

However, chitosan is generally soluble in an acid environment. Thus, the films obtained from acid solutions based on chitosan are still highly laden with salts and still have their acid character. A chitosan film obtained from an acidic solution of chitosan can thus degrade and disintegrate when it is brought in contact with water or biological fluids. Therefore it can no longer perform its function of haemostatic barrier.

Accordingly, in order to be used in medical devices, especially in haemostatic patches, chitosan films must be neutralized. Generally this neutralization is obtained by treating these films with a strong base such as sodium hydroxide.

However, this treatment with sodium hydroxide can affect the integrity of the part of the patch supporting the chitosan film: thus, in the case of a haemostatic patch with an absorbent porous layer based on oxidized cellulose, treatment of the chitosan barrier film with sodium hydroxide would destroy the porous layer of oxidized cellulose.

Thus, it would be desirable to employ a method of preparing a haemostatic patch comprising a porous layer based on oxidized cellulose and a barrier film based on chitosan, which would avoid the phenomenon of degradation of the porous layer during the necessary neutralization of the chitosan film.

SUMMARY

The present invention relates to a method of preparing a haemostatic patch comprising a porous layer based on oxidized cellulose and a neutralized film based on chitosan, said film comprising a free face and a face fixed on one of the faces of the porous layer, comprising the following steps:

a°) preparing a porous layer based on oxidized cellulose, b°) preparing a film based on chitosan starting from an acidic aqueous solution of chitosan, c°) fixing the film obtained in b°) on one face of the porous layer, d°) neutralizing the film obtained in b°), where step c°) can be carried out before or after step d°), characterized in that:

the neutralizing step d°) comprises treatment of said film with a neutralizing composition comprising at least ethanol and ammonium hydroxide ($NH_4OH$).

With the method according to the invention it is possible to obtain haemostatic patches based on a porous layer of oxidized cellulose and a chitosan barrier film without the risk of the chitosan film dissolving in contact with biological fluids, in particular in contact with blood. According to the method of the invention, firstly a film based on chitosan is manufactured starting from an acidic solution, then this film, alone or already fixed on the porous layer based on oxidized cellulose, is treated in order to neutralize it and obtain a final product usable in contact with biological fluids, without destroying the porous layer to which this film is attached. Regardless of the order of steps) c°) and d°) of the method according to the invention, the neutralizing composition of the method of the invention, comprising at least ethanol and ammonium hydroxide ($NH_4OH$), makes it possible to neutralize the chitosan-based film without damaging the porous layer based on oxidized cellulose. In particular, neutralization by means of a neutralizing composition comprising at least ethanol and ammonium hydroxide ($NH_4OH$) makes it possible to neutralize the chitosan-based film both at the surface and throughout its thickness, whether or not it is already fixed to the porous layer based on oxidized cellulose, without damaging said porous layer. With the method of the invention, it is possible to obtain a haemostatic patch having a film of neutralized chitosan as barrier, with a porous layer fixed to this film, said porous layer being based on oxidized cellulose, or said porous layer consisting of oxidized cellulose.

The present invention further relates to a haemostatic patch comprising a porous layer based on oxidized cellulose and a film based on chitosan fixed to one face of said porous layer, characterized in that said film is in neutralized form.

The present invention further relates to a haemostatic patch obtained by the method herein described, comprising a porous layer based on oxidized cellulose and a film based on chitosan fixed to one face of said porous layer, characterized in that said film is in neutralized form.

In one embodiment of the invention, the treatment in step d°) comprises a succession of operations of contacting at least the face that is free, or is intended to be free, of the film with said neutralizing composition. For example, if the film is fixed to the porous layer before it is neutralized, the treatment in step d°) will essentially consist of contacting only the free face of the film with the neutralizing composition, preferably without contacting the porous layer, on which the film will already be fixed: in fact, contact of the porous layer with the neutralizing composition could affect the integrity of the latter. Alternatively, if the film is neutralized before being fixed to the porous layer, the treatment in step d°) can comprise immersing the whole film, i.e. both of its faces, in a bath of the neutralizing composition. In both cases, the chitosan-based film is neutralized effectively at the surface and through its thickness, and the integrity of the porous layer is unaffected by the neutralizing composition comprising ethanol and ammonium hydroxide ($NH_4OH$).

In one embodiment of the invention, step d°) further comprises a step of washing of said face of said film that is free, or intended to be free, after said treatment with the neutralizing composition. For example, the washing step comprises one or more operations of rinsing of at least said face of said film that is free, or intended to be free, with an ethanol/water composition followed by washing with water. Thus, if the film is fixed to the porous layer before it is neutralized, only its free face will be washed after application of the neutralizing composition. Alternatively, if the film is neutralized before being fixed on the porous layer, the whole film can be immersed in an ethanol/water composition and/or in water.

In one embodiment of the invention, the fixing step c°) is carried out before the neutralizing step d°). In such a case, for example, according to step b°), the acidic aqueous solution of chitosan is poured into a mould in the form of one or more layers, which are left to dry by evaporation of the water from said solution in order to obtain a film, then, according to step c°), before the end of the drying step of step b°), one face of the porous layer of oxidized cellulose is deposited on said film, complete drying of the film thus resulting in fixation of the porous layer on the film. In fact, when the porous layer is deposited on the film that is still in the course of drying, it penetrates superficially into the film under the action of the force of gravity. Thus, as drying is completed, the film traps the portion of the porous layer that has thus sunk slightly, thus providing fixation of the porous layer on the film. According to this embodiment of the invention, the treatment in step d°) comprises application of said neutralizing composition on the free face of the film, said neutralizing composition further comprising water. In such an embodiment of the invention, said neutralizing composition can for example consist of an ethanol/water/ammonium hydroxide mixture in the proportions 80/16/14 by weight. This formulation for the neutralizing composition of the method of the invention makes it possible to achieve effective neutralization of the film on its surface and through its thickness while avoiding causing shrinkage of the film, without damaging the integrity of the porous layer on which the film is already fixed.

In such an embodiment of the invention, for example, the neutralizing composition is applied on the free face of the film one or more times using a brush. For example, the bristles of a brush are soaked in neutralizing composition consisting of an ethanol/water/ammonium hydroxide mixture in the proportions 80/16/14 by weight and the free face of the film is brushed: several passes of the brush can be carried out, for example 3 passes. The film is thus neutralized. The film is then washed, as described above: for example, another brush is used, which is soaked with an ethanol/water composition, for example in the proportions 50/50 by weight. Several passes of the brush can be carried out, for example three. A last pass with a brush soaked in just water can be carried out to finalize the washing.

In another embodiment of the invention, the neutralizing step d°) is carried out before the fixing step c°). In such a case, for example, according to step b°), the acidic aqueous solution of chitosan is poured into a mould in the form of one or more layers, which are left to dry by evaporation of the water until a film is obtained, which is removed from the mould, then, according to step d°), the treatment of the film obtained in b°) comprises immersing said film in said neutralizing composition, preferably for 30 minutes. In such an embodiment, for example, once the film is completely dry and can be handled, it is immersed completely in a bath of neutralizing composition. Thus, in such a case, both faces of the film are treated with the neutralizing composition. In such an embodiment of the invention, the neutralizing composition can consist of an ethanol/ammonium hydroxide mixture in the proportions 80/20 by weight. This formulation for the neutralizing composition of the method of the invention makes it possible to carry out effective neutralization of the film without damaging the integrity of the porous layer when the film is to be fixed on the porous layer in the next step.

After immersion in a bath of the neutralizing composition as described above, the chitosan-based film is thus neutralized. The film can then be washed, as described above: for example, the film is immersed one or more times in baths of an ethanol/water composition, for example in the proportions 50/50 by weight, until a pH close to 7 is obtained for the washing baths. The film can then be submitted to a last bath of water only, to finalize the washing.

In such an embodiment, according to step c°), the neutralized film obtained at the end of step d°) can be fixed on one face of the porous layer of oxidized cellulose by means of a glue obtained starting from an acidic solution of chitosan. For example, said glue is spread on one face of the porous layer and/or on the face of the film intended to be fixed to the porous layer, and the film is fixed to the porous layer by application of the film on said face of the porous layer with pressure. The integrity of the porous layer based on oxidized cellulose is not affected during this fixing step.

Regardless of the order of steps c°) and d°) described above, a plasticizer, for example glycerol, can be added to the acidic aqueous solution of chitosan intended to form said chitosan-based film. With such an embodiment, a chitosan film can finally be obtained that has excellent mechanical properties.

In one embodiment of the invention, the porous layer is a textile, preferably a three-dimensional knitted fabric. Said porous layer, in the form of three-dimensional knitted fabric, gives excellent absorption of biological fluids, especially of blood.

BRIEF DESCRIPTION OF THE DRAWINGS

The invention and its advantages will become clearer from the following detailed description and the drawings in which.

DETAILED DESCRIPTION

Figure 1A:
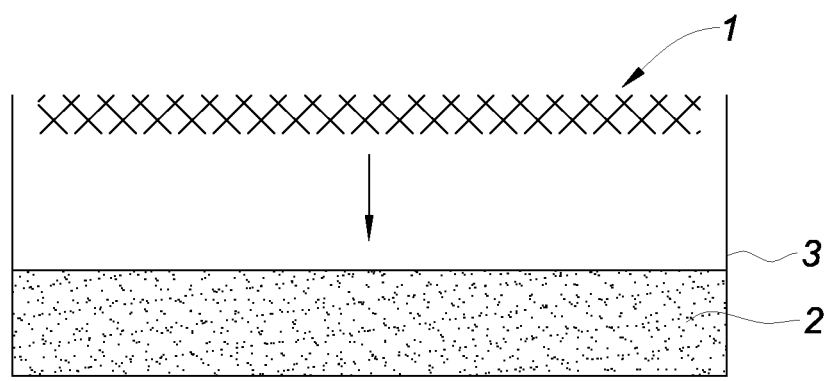
FIGS. 1A-1C are sectional views showing the various steps of a first implementation of the method according to the invention.

According to a first step of the method according to the invention, step a°), a porous layer based on oxidized cellulose is provided. "Based on oxidized cellulose" means, according to the present application, that the main component of the porous layer is oxidized cellulose. The porous layer can further comprise other biocompatible, preferably bioabsorbable, materials. For example, the porous layer can comprise, as other bioabsorbable materials, synthetic polymers such as polylactic acid and/or polymers of natural origin such as chitosan.

Oxidized cellulose is a known bioabsorbable material. It can for example be selected from oxidized cellulose, where the $C_6$ primary alcohol is partially or fully oxidized to carboxylic acid, for example to give polyglucuronic acid, oxidized cellulose in the form of polyaldehydes by periodic acid, and mixtures thereof. The cellulose used for oxidation can be obtained from type I cellulose or can be regenerated.

Several types of regenerated cellulose have been developed industrially. We may mention for example the "viscose" process, which is based on the solubility of cellulose xanthate in a dilute solution of sodium hydroxide. We may also mention the so-called "cupro-ammonium process" employed for example by the company Bemberg in Italy or the company Asahi Chemical Industries in Japan, which consists of dissolving cellulose in an ammoniacal solution of copper. Another method of preparing regenerated cellulose suitable for the present invention is the method of organic-phase dissolution of cellulose by N-methylmorpholine oxide (N.M.M.O.), called the "Lyocell® process", employed for example by the company Lenzing in Austria.

In the present application, "porous layer" means a layer having pores, or voids, cells, holes, orifices, distributed regularly or irregularly, not only on the surface but also within the thickness of said layer, and more or less interconnected. Said porous layer is particularly effective for absorbing biological fluids such as blood.

In one embodiment, the porous layer based on oxidized cellulose is in the form of a textile openwork based on oxidized cellulose.

According to the present application, "textile" means any arrangement or assemblage of biocompatible threads, fibres, filaments and/or multifilaments, for example obtained by knitting, weaving, braiding, or alternatively non-woven. The arrangement of threads of the textile according to the invention defines at least two opposite faces, a first face and a second face.

In the present application, "textile openwork" means any textile whose arrangement of threads of which it is constituted determines openings, cells or voids in the thickness of the textile and on the faces of the textile, and these openings, cells or voids can constitute channels with openings on either side of the textile. This textile openwork gives good absorption of biological fluids.

The textile can be in the form of a two-dimensional or three-dimensional knitted fabric.

"Two-dimensional knitted fabric" means, in the sense of the present application, a knitted fabric having two opposite faces joined together by stitches but lacking cross-members giving it a certain thickness: a knitted fabric of this kind can be obtained for example by knitting threads on a warp knitting machine or Raschel machine using two guide bars. Examples of knitting of two-dimensional knitted fabrics suitable for the present invention are given in document WO2009/071998.

"Three-dimensional knitted fabric" means, according to the present application, a knitted fabric having two opposite faces joined together by a cross-member giving the knitted fabric a significant thickness, said cross-member itself being formed of additional connecting threads supplementary to the threads forming the two faces of the knitted fabric. This knitted fabric can be obtained for example on a warp knitting machine or double-bed Raschel machine using several guide bars. Examples of knitting of three-dimensional knitted fabrics suitable for the present invention are given in documents WO99/05990, WO2009/031035, WO2009/071998.

This kind of three-dimensional knitted fabric, with the presence of a cross-member giving it a significant thickness, provides excellent absorption of biological fluids such as blood and is particularly suitable for manufacture of the haemostatic patch of the invention.

A knitted fabric, in particular three-dimensional, based on oxidized cellulose, can be obtained by knitting firstly threads of unoxidized regenerated cellulose, then submitting the knitted fabric thus obtained to oxidation.

In fact, when spun through a perforated plate, viscose sets in an acid medium and forms long continuous filaments of regenerated cellulose, which are dried and combined in multifilament threads. A regenerated cellulose thread is obtained that has good mechanical strength.

Generally this regenerated cellulose thread is not absorbable. However, it has good mechanical strength allowing it to be used for manufacturing a knitted fabric. As an example, we may mention, as regenerated cellulose thread suitable for manufacturing a knitted fabric suitable for the porous layer of the patch of the invention, the 90 decitex multifilament thread marketed under the name "CUPRO® Cusio" by the Italian company Bemberg.

The knitted fabric obtained is then oxidized in order to form a porous layer based on oxidized cellulose suitable for the haemostatic patch and for the method of preparing said patch according to the present invention.

In a preferred embodiment of the method of the invention, the porous layer based on oxidized cellulose is a three-dimensional knitted fabric made from oxidized cellulose.

According to a second step of the method according to the invention, step b), a film based on chitosan is prepared starting from an acidic aqueous solution of chitosan.

"Based on chitosan" means, according to the present application, that the main component of the film is chitosan. The chitosan-based film can further comprise other compounds. For example, the chitosan-based film can comprise a plasticizer, for example glycerol, to improve the mechanical properties of the film.

Chitosan is a biocompatible biopolymer obtained by deacetylation of chitin. Chitin is extracted from exoskeletons of arthropods such as the lobster, crab, prawn, the endoskeleton of cephalopods such as the squid, or from fungi. Extraction of chitin involves steps of hydrolysis of the proteins and lipids, depigmentation and demineralization. Hydrolysis of the proteins and lipids is usually carried out in the presence of sodium hydroxide, and demineralization requires the use of hydrochloric acid.

Once the chitin has been extracted, chitosan is obtained by a deacetylation step, which consists of hydrolysis of the acetamide groups. This reaction is generally carried out at high temperature in an alkaline solution, for example a 48% solution of sodium hydroxide (NaOH) in water, at 90° C.

Chitosan is a compound that is soluble in aqueous solution and can have a degree of acetylation (DA) of up to 70%.

The following publications describe processes for deacetylation of chitin to obtain chitosan: "Lamarque, G., C. Viton, and A. Domard, *New Route of Deacetylation of α- and β-Chitins by means of Freeze-Pump Out-Thaw Cycles*. Biomacromolecules, 2005. 6 (3): p. 1380-1388.", "Lamarque, G., C. Viton, and A. Domard, *Comparative Study of the First Heterogeneous Deacetylation of α- and β-Chitins in a Multistep Process*. Biomacromolecules, 2004. 5 (3): p. 992-1001.", "Lamarque, G., C. Viton, and A. Domard, *Comparative Study of the Second and Third Heterogeneous Deacetylations of α- and β-Chitins in a Multistep Process*. Biomacromolecules, 2004. 5 (5): p. 1899-1907.", "Tolaimate, A., et al., *Contribution to the preparation of chitins and chitosans with controlled physicochemical properties*. Polymer, 2003. 44 (26): p. 7939-7952."

Chitosan is a bioabsorbable compound. The degree of acetylation of chitosan can have an influence on the kinetics of degradation of chitosan. Thus, depending on the kinetics of biodegradation desired for the film of the haemostatic patch prepared according to the method of the invention, the chitosan will have to have a degree of acetylation of 2, 10, 20, 30, 40, 50, 60 or 70%.

In one embodiment of the method according to the invention, the degree of acetylation of the chitosan ranges from 2 to 70%. With this chitosan it is possible to obtain a film having optimum degradation kinetics for the manufacture of haemostatic patches.

The chitosan solution in step b) of the method according to the invention is generally prepared starting from a solution of chitosan in water, with the concentration of chitosan in said solution ranging for example from 0.25% to 10%, by weight, relative to the total weight of the solution, to which an acid is added in stoichiometric proportion, said acid being selected for example from acetic acid, hydrochloric acid and mixtures thereof. For a chitosan of molecular weight 500 000 Da (500 000 g/mol), for example, the concentration of chitosan in the starting aqueous solution can range from 0.25% to 5%, by weight, relative to the total weight of the solution.

With these chitosan concentrations it is possible to obtain, finally, a film that has good mechanical properties.

In one embodiment of the method according to the invention, the pH of the acidic aqueous solution of chitosan is from 2.5 to 5.5.

In order to form the chitosan-based film of the method of the invention, the acidic aqueous solution of chitosan is poured into a mould in order to form a layer. The acidic aqueous solution can be cast in the mould in the form of one or more layers, depending on the final thickness that is desired for the barrier film of the haemostatic patch. Generally, the mould is of rectangular shape having dimensions compatible with the use of the film obtained as part of a haemostatic patch.

The layer or layers of acidic aqueous solution are left to dry for evaporation of the water present in the acidic aqueous starting solution. Generally this drying step is carried out under a laminar-flow hood.

Drying of the layer or layers of acidic aqueous solution by evaporation of the water as stated above will make it possible to obtain the chitosan-based film used in the method according to the invention.

During step b°) of formation of the chitosan-based film, the water of the acidic aqueous starting solution is evaporated but the acid remains in the film. The film obtained is therefore of an acidic character. This film cannot be used as it is for forming the barrier of the haemostatic patch of the invention, as it would disintegrate very rapidly merely in contact with biological fluids.

Thus, besides a step of fixing the film to the porous layer based on oxidized cellulose, the method according to the invention comprises a step of neutralizing the film obtained in b°), and this neutralizing step can be carried out before or after the fixing step.

In the rest of the description, a first embodiment of the method according to the invention will be described first, according to which, firstly, the film is fixed to the porous layer based on oxidized cellulose, then it is neutralized, while it is already fixed on the porous layer based on oxidized cellulose. A second embodiment of the method according to the invention will then be described, according to which the film is neutralized first, then it is fixed to the porous layer based on oxidized cellulose.

According to the first embodiment of the method according to the invention, before the end of the drying step in step b°) of formation of the film, the porous layer of oxidized cellulose, in particular the three-dimensional knitted fabric, is deposited on the last layer of acidic aqueous solution based on chitosan that is cast. Under the action of gravity, the porous layer, for example the three-dimensional knitted fabric, penetrates superficially within the last layer cast that is drying. In final drying by evaporation of the water that remains in the last layer cast, the film traps the portion of the porous layer, for example of the three-dimensional knitted fabric, that had slightly penetrated into said last layer cast, and the porous layer is thus fixed to the film.

In the case when the film is fixed to the porous layer before it is neutralized, the neutralizing treatment is carried out on the face of the film that has been left free, i.e. on the face of the film that is not attached to the porous layer, in particular to the textile or knitted fabric based on oxidized cellulose.

In this first embodiment of the invention, for example, the neutralizing composition is applied on the free face of the film one or more times with a brush, taking care that the neutralizing composition does not come in contact with the porous layer based on oxidized cellulose. For example, the bristles of a brush are soaked with neutralizing composition consisting of an ethanol/water/ammonium hydroxide mixture in the proportions 80/16/14 by weight and the free face of the film is brushed or painted: several passes of the brush can be carried out, for example 3 passes. This formulation for the neutralizing composition makes it possible to avoid shrinkage of the film during this neutralizing step. Moreover, said formulation for the neutralizing composition and said number of passes make it possible to carry out effective neutralization of the chitosan-based film, both at the surface and throughout its thickness, without damaging the integrity of the porous layer on which the film is already fixed. The film thus loses its acid character and is neutralized.

The film can then be washed: for example, another brush is used, which is soaked with an ethanol/water composition, for example in the proportions 50/50 by weight, and which is brushed over the free face of the film, still without contacting the porous layer, for example the three-dimensional knitted fabric, based on oxidized cellulose. Several passes of the brush can be carried out, for example three, or up to five. A last pass with a brush soaked in water only can be carried out to finalize the washing.

According to the second embodiment of the method according to the invention, the cast layers of acidic aqueous solution from step b°) of formation of the thread are left to dry by complete evaporation of the water and until a film is obtained that can easily be removed from the mould and handled.

The chitosan-based film thus obtained, which has not been neutralized, can be submitted to one or more operations of immersion in baths of said neutralizing composition. For example, the film can be immersed in a bath of neutralizing composition preferably for 30 minutes. Thus, in this second embodiment of the method according to the invention, both faces of the chitosan-based film are treated with the neutralizing composition. In such an embodiment of the invention, the neutralizing composition can consist of an ethanol/ammonium hydroxide mixture in the proportions 80/20 by weight. This formulation for the neutralizing composition of the method of the invention makes it possible to carry out effective neutralization of the film, both on the surface of the film and in its thickness, without damaging the integrity of the porous layer during the next step of fixation of the film on the porous layer based on oxidized cellulose.

After immersion in a bath of the neutralizing composition as described above, the chitosan-based film has lost its acid character and it is neutralized. The film can then be washed: for example, the film is immersed one or more times in baths of an ethanol/water composition, for example in the proportions 50/50 by weight, until a pH close to 7 is obtained for the washing baths. The film can then be submitted to a last bath of water only to finalize the washing.

In this second embodiment, according to step c°), the neutralized film obtained at the end of step d°) can be fixed on one face of the porous layer of oxidized cellulose, for example on the three-dimensional knitted fabric, by means of a glue obtained starting from an acidic solution of chitosan. For example, said glue is spread on one face of the porous layer and/or on the face of the film intended to be fixed to the porous layer, and the film is fixed to the porous layer by application of the film on said face of the porous layer with pressure. The integrity of the porous layer based on oxidized cellulose is not affected during this fixing step.

Regardless of which embodiment described above is used, a patch is obtained comprising a porous layer based on oxidized cellulose, for example a three-dimensional knitted fabric, and a film based on chitosan fixed to one face of this porous layer, the film being in neutralized form. This patch can be used effectively as a haemostatic patch for stopping effusion of blood during a surgical operation. Moreover, this patch can be completely bioabsorbable: it can thus disappear in the weeks following its implantation, for example in less than 4 weeks, once its haemostatic function is no longer required. This thus avoids introducing a foreign body into a patient's body permanently.

EXAMPLES

Example 1

Figure 1B:
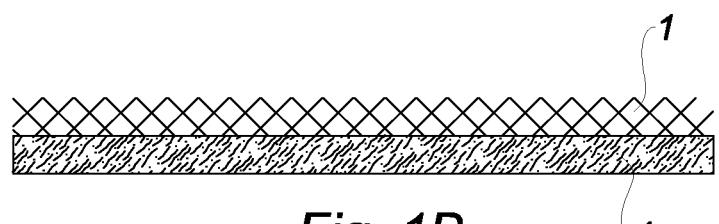
Figure 1C:
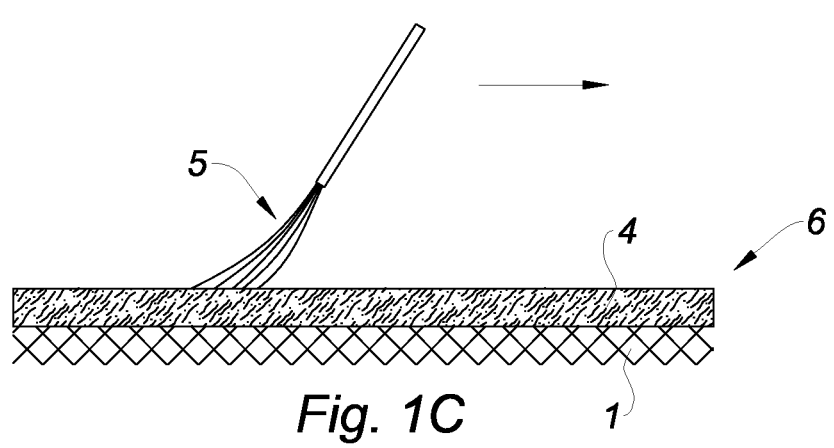

The fixation of a film based on neutralized chitosan on a textile of oxidized cellulose is described in the present example, referring to FIGS. 1A-1C.

A textile of oxidized cellulose 1, which is a porous three-dimensional knitted fabric, as shown in FIG. 1A, is provided. This textile is bioabsorbable.

An acidic solution based on chitosan is prepared by adding acetic acid in stoichiometric proportions to a solution of chitosan with a degree of acetylation of 50% and with a molecular weight of 550 000 Da at 10 wt % in water. 25 wt % of glycerol is added. The presence of glycerol in the acidic starting solution of chitosan then makes it possible to obtain a film that has good mechanical properties.

The acidic solution thus obtained 2 is poured into a rectangular mould 3 as shown in FIG. 1A: for example, from 8 to 30 ml of acidic solution is poured into a mould with dimensions of 10×15 cm. After evaporation of the water present in the solution, a film is obtained.

The solution can be cast in the mould in the form of several successive layers so that a thicker film is finally obtained. For example, three successive layers of acidic solution can be cast.

Before drying the last layer cast of the acidic solution 2, one face of the textile of oxidized cellulose 1, cut to the dimensions of the mould, is deposited on this layer as shown in FIG. 1. Thus, during drying of the last layer cast, the textile becomes fixed to the film obtained once the water has evaporated. A textile of oxidized cellulose 1 with a film 4 of chitosan fixed on one of its faces is thus obtained, as shown in FIG. 1B. At this stage, the chitosan film still has an acidic character and has not been neutralized.

A neutralizing composition is prepared, consisting of an ethanol/water/ammonium hydroxide mixture in the proportions 80/16/14 by weight. A brush 5 is soaked with this neutralizing composition and is applied on the free face of the chitosan film 4, i.e. on the face of the chitosan film which is not attached to the textile of oxidized cellulose 1, as shown in FIG. 1C.

During said application, care is taken not to bring the textile of oxidized cellulose 1 into contact with the neutralizing composition.

The neutralizing composition is applied on said face of the film at least three times. This formulation for the neutralizing composition makes it possible to avoid shrinkage of the film during this neutralizing step.

The neutralization is effective: the film can then be washed with aqueous solutions without risk of redissolving.

Thus, the neutralized film is rinsed by application of a brush soaked in an ethanol/water mixture in proportions of 50/50 by weight. This mixture can be applied several times, preferably up to three times. The film is then washed with water (100% water), either by application of a brush soaked with water, or by immersing in a water bath.

We thus obtain a textile of oxidized cellulose with a chitosan film fixed on one of its faces, said film having been neutralized. With the method of the invention, the textile of oxidized cellulose has not been damaged by the step of neutralization of the chitosan film and this textile has preserved its integrity. Moreover, the chitosan-based film has kept its initial dimensions, even after neutralization.

The textile thus obtained, with one of its faces covered with a film of neutralized chitosan, can be used as haemostatic patch 6 and can be implanted in a human body without risk of the chitosan film disintegrating and disappearing in contact with biological fluids.

The textile part, which is a three-dimensional knitted fabric of oxidized cellulose 1, thus forms a porous layer capable of absorbing blood. The film of neutralized chitosan, for its part, does not degrade in contact with biological fluids, and it acts as a haemostatic barrier.

The whole patch 6, namely the textile part and the film, is bioabsorbable and disappears in less than 4 weeks after implantation.

Said patch 6 is particularly useful for stopping effusions of blood during surgery. Said patch is completely bioabsorbable and disappears in less than 4 weeks after implantation, when its haemostatic function is no longer required.

Example 2

The fixation of a film based on neutralized chitosan to a textile of oxidized cellulose is described in the present example, referring to FIGS. 2A-2E.

An acidic solution based on chitosan is prepared by adding acetic acid in stoichiometric proportions to a solution of chitosan with a degree of acetylation of 50% and a molecular weight of 550 000 Da at 10 wt % in water. 25 wt % of glycerol is added. The presence of glycerol in the acidic starting solution of chitosan then makes it possible to obtain a film that has good mechanical properties.

Figure 2A:
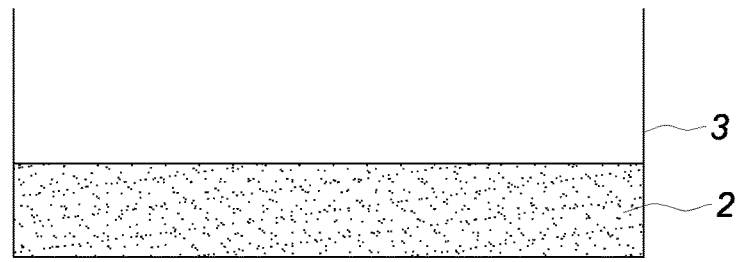
FIGS. 2A-2E are sectional views showing the various steps of a second implementation of the method according to the invention.
Figure 2B:

The acidic solution 2 thus obtained is poured into a rectangular mould 3 as shown in FIG. 2A: for example, from 8 to 30 ml of acidic solution is poured into a mould with dimensions of 10×15 cm. After evaporation of the water present in the solution, a film 4 is obtained, as shown in FIG. 2B.

The solution can be cast in the mould in the form of several successive layers so that a thicker film is finally obtained. For example, three successive layers of acidic solution are cast.

The layers are left to dry until the water has evaporated completely and a dry film 4 is obtained (FIG. 2B), which can easily be manipulated by hand. For example, the layers are left to dry for 2 h at room temperature.

Figure 2C:
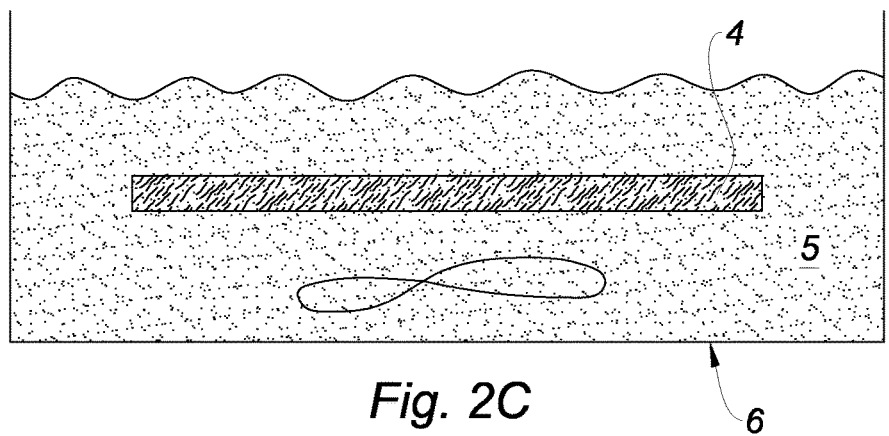

The chitosan film 4 obtained is of an acid character and has not been neutralized. In order to neutralize it, it is immersed in a neutralizing composition 5 consisting of an ethanol/ammonium hydroxide mixture in the proportions 80/20 by weight: for example, film 4 is immersed in said composition for 30 minutes in an orbital stirrer 6, as shown in FIG. 2C.

The neutralization is effective: the film can then be washed in aqueous solutions without risk of redissolving.

Thus, the neutralized film is rinsed by successive operations of immersion, for example three times, in baths of an ethanol/water mixture in proportions of 50/50 by weight until a pH of 7 is obtained for the rinsing mixture. The film is then washed by immersing in a water bath (100% water).

The film is then left to dry in spread-out form to avoid the formation of creases in the film.

The film of neutralized chitosan thus obtained 7 is then fixed on one face of a textile of oxidized cellulose by means of a glue based on chitosan as explained below, referring to FIGS. 2D and 2E.

To prepare the glue, acetic acid is added in stoichiometric proportions to a solution of chitosan with a degree of acetylation of 50% and a molecular weight of 550 000 Da at 10 wt % in water.

Figure 2D:

The glue obtained 8 is spread on one face of the film of neutralized chitosan 7 as shown in FIG. 2D. Alternatively, the glue could be spread on the face of the textile for fixing to the film, or both on one face of the film and on the face of the textile to be attached to the film.

Figure 2E:
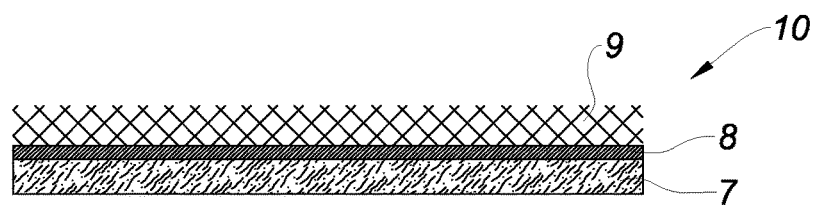

A textile of oxidized cellulose 9 is provided, which is a porous three-dimensional knitted fabric as shown in FIG. 2E. This textile is bioabsorbable.

The textile of oxidized cellulose 9 is applied with pressure on the glue 8, as shown in FIG. 2E, and the film 7 of neutralized chitosan is thus fixed to the textile 9.

The "textile+film" assembly can then be dried under a laminar-flow hood.

A textile of oxidized cellulose is thus obtained with a chitosan film fixed on one of its faces, said film having been neutralized. With the method of the invention, the textile of oxidized cellulose has not been damaged by the step of neutralization of the chitosan film and this textile has preserved its integrity. Moreover, the chitosan-based film has a good, smooth and crease-free appearance.

The textile thus obtained, with one of its faces covered with a film of neutralized chitosan, can be used as haemostatic patch 10 and can be implanted in a human body without risk of the chitosan film 7 disintegrating and disappearing in contact with biological fluids.

The textile part, which is a three-dimensional knitted fabric of oxidized cellulose, thus forms a porous layer capable of absorbing blood. The film of neutralized chitosan, for its part, does not degrade in contact with biological fluids, and it acts as a haemostatic barrier.

The whole of patch 10, namely the textile part and the film, is bioabsorbable and disappears in less than 4 weeks after implantation.

Said patch 10 is particularly useful for stopping effusions of blood during surgery. This patch is completely bioabsorbable and disappears in less than four weeks after implantation, when its haemostatic function is no longer required.

What is claimed is:

1. A method of preparing a haemostatic patch comprising a porous layer including oxidized cellulose and a film including neutralized chitosan, the film comprising a first free face and a second face fixed on a first face of the porous layer, comprising the following steps:
    a) preparing a porous layer including oxidized cellulose,
    b) preparing a film including chitosan starting from an acidic aqueous solution of chitosan,
    c) fixing the film obtained in b) on a face of the porous layer,
    d) neutralizing the film obtained in b), wherein step c) is carried out before or after step d) and the neutralizing step d) comprises treating the film with a neutralizing composition comprising at least ethanol and ammonium hydroxide.

2. The method according to claim 1, wherein step d) comprises a succession of operations of contacting at least the first free face of the film with the neutralizing composition.

3. The method according to claim 1, wherein step d) further comprises washing the first free face of the film after treating with the neutralizing composition.

4. The method according to claim 3, wherein the washing comprises one or more operations of rinsing at least the first free face of the film with a composition comprising ethanol and water followed by a washing with water.

5. The method according to claim 1, wherein step c) is carried out before step d).

6. The method according to claim 1, wherein step b) comprises pouring the acidic aqueous solution of chitosan into a mold as at least one layer, and drying the at least one layer by evaporation of water from the acidic aqueous solution to obtain the film.

7. The method according to claim 6, wherein step c) comprises depositing the face of the porous layer of oxidized cellulose on the film prior to the drying of step b) being complete, and allowing the film to dry completely to provide fixation of the porous layer on the film.

8. The method according to claim 7, wherein step d) comprises applying the neutralizing composition to the first free face of the film and the neutralizing composition further comprises water.

9. The method according to claim 8, wherein the neutralizing composition consists of an ethanol/water/ammonium hydroxide mixture in a proportion of 80/16/14 by weight.

10. The method according to claim 7, wherein step d) comprises applying the neutralizing composition on the first free face of the film one or more times using a brush.

11. The method according to claim 1, wherein step d) is carried out before step c).

12. The method according to claim 11, wherein step b) comprises pouring the acidic aqueous solution of chitosan into a mold as at least one layer, and drying the at least one layer by evaporation of water from the acidic aqueous solution until the film is obtained and removed from the mold.

13. The method according to claim 12, wherein step d) comprises immersing the film obtained in step b) in the neutralizing composition.

14. The method according to claim 13, wherein the film obtained in step b) is immersed in the neutralizing composition for 30 minutes.

15. The method according to claim 13, wherein the neutralizing composition consists of an ethanol/ammonium hydroxide mixture in a proportion of 80/20 by weight.

16. The method according to claim 13, wherein step c) comprises fixing the film obtained at the end of step d) on the face of the porous layer of oxidized cellulose by using a glue comprising an acidic solution of chitosan.

17. The method according to claim 16, wherein the glue is spread on the face of the porous layer and/or on the second face of the film intended to be fixed to the porous layer, and the film is fixed to the porous layer by application of the film on the face of the porous layer with pressure.

18. The method according to claim 1, wherein the acidic aqueous solution of chitosan of step b) further comprises a plasticizer.

19. The method according to claim 18, wherein the plasticizer comprises glycerol.

20. The method according to claim 1, wherein the porous layer is a textile.

21. The method according to claim 1, wherein the porous layer is a three-dimensional knitted fabric.

22. A haemostatic patch obtained by the method according to claim 1, comprising a porous layer including oxidized cellulose and a film including chitosan fixed to one face of the porous layer, wherein the film is in a neutralized form.

* * * * *